United States Patent [19]

Mues et al.

[11] Patent Number: 4,851,550
[45] Date of Patent: Jul. 25, 1989

[54] PROCESS FOR THE PREPARATION OF CYCLIC ALIPHATIC ORTHOCARBONIC ESTERS NEW CYCLIC ORTHOCARBONIC ESTERS

[75] Inventors: Peter Mues; Hans-Josef Buysch, both of Krefeld, Fed. Rep. of Germany

[73] Assignee: Bayer Aktiengesellschaft, Leverkusen, Fed. Rep. of Germany

[21] Appl. No.: 99,287

[22] Filed: Sep. 21, 1987

Related U.S. Application Data

[63] Continuation of Ser. No. 816,660, Jan. 7, 1986, abandoned.

[30] Foreign Application Priority Data

Jan. 23, 1985 [DE] Fed. Rep. of Germany ....... 3502106

[51] Int. Cl.$^4$ .......................................... C07D 317/12
[52] U.S. Cl. .................................. 549/334; 549/335; 549/347
[58] Field of Search ............................... 549/334, 335

[56] References Cited

FOREIGN PATENT DOCUMENTS 1907197 10/1969 Fed. Rep. of Germany .
0100582 6/1985 Japan .................................... 549/335
1289091 12/1986 Japan .................................... 549/335

OTHER PUBLICATIONS

J. Hocker: Orthokohlensaure-Derivate Ohne Halogen-Funktion, pp. 699–703.
Annalen Der Chemie Justus Liebigs Band 675 Seiten 1–212 Herausgegeben Von Richard Kuhn, Aug. 5, 1954, pp. 142–143.
Mues et al., "Cyclic Aliphatic Orthoformates", CA 105, 191103e (1986).
Endo et al., "Spiroorthocarbonates", CA 98 160691c (1983).
Takekoshi II, "Polyorthocarboxate Polymers and Co-polymers", CA 71 125214v (1969).
Gross et al., Chem. Berichte, vol. 94 (1961), pp. 544–550.
Takekoshi III, Polym. Prepr, Amer. Chem. Soc., Div. Polym. Chem. (1969, vol. 10(1), pp. 103–110.
Takekoshi IV, J. Polym. Sci., Polym. Chem. Ed. (1972), vol. 10(12), pp. 3509–3518.

Primary Examiner—Glennon H. Hollrah
Assistant Examiner—A. A. Owens
Attorney, Agent, or Firm—Sprung Horn Kramer & Woods

[57] ABSTRACT

The process according to the invention is particularly suitable for the preparation of aliphatic spiroorthocarbonates. For the preparation of aliphatic spiroorthocarbonates of the formula

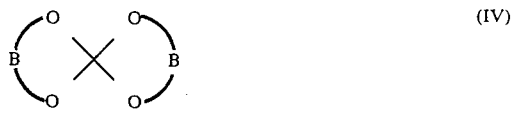

(IV)

in which dichloromethane derivatives of the formula

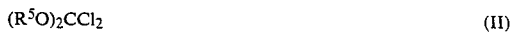

$(R^5O)_2CCl_2$ (II)

are reacted with aliphatic diols of the formula

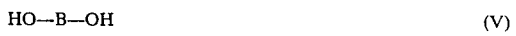

HO—B—OH (V)

in the presence of stoichiometric amounts of H-containing bases, which contain the nitrogen as part of an aromatic system.

1 Claim, No Drawings

PROCESS FOR THE PREPARATION OF CYCLIC ALIPHATIC ORTHOCARBONIC ESTERS NEW CYCLIC ORTHOCARBONIC ESTERS

This is a continuation of application Ser. No. 816,660, filed Jan. 7, 1986 now abandoned.

The present invention relates to a process for the preparation of cyclic, aliphatic orthocarbonic esters and to new cyclic orthocarbonic esters.

Although cyclic, aliphatic orthocarbonic esters, in particular aliphatic spiroorthocarbonates, represent an interesting class of substances, to date only five methods of preparation of the spiroorthocarbonates have been disclosed: reaction of di-thallium(I) glycolates with $CS_2$, with elimination of thallium sulphide (J. Org. Chem. 37, 4198 (1972)); reaction of 0,0'-bis(tributylstannyl) derivatives of glycols with $CS_2$, with elimination of bis(tributyltin) sulphide (J. Org. Chem. 35, 2347 (1970)); reaction of alkanediyl dioxydibutylstannanes with $CS_2$ (J. Org. Chem. 36, 1176 (1971)); reaction of orthocarbonic esters with diols, with elimination of alcohol (DE-OS (German Published Specification) No. 3,225,818; synthesis 1984, 837) and reaction of epoxides with cyclic five- or six-membered carbonates in the presence of boron trifluoride etherate (DE-OS (German Published Specification) No. 3,406,049).

Although the first three of the processes mentioned take place with reasonably good yields, it is necessary to use costly organometallics and toxic $CS_2$. In the last of these processes a costly tetraalkoxymethane is used as the starting material, and the removal of the product from the neutralized catalyst is not without its problems and apparently determines the yield; catalyzed addition of epoxides onto carbonate takes place only in very poor yields.

A process for the preparation of cyclic, aliphatic orthocarbonic esters of the formula $$\begin{array}{c}\diagup O \diagdown \diagup OR^1 \\ A \diagdown O \diagup \diagdown OR^2 \end{array} \quad (I)$$

in which
A represents $$\begin{array}{cc} R^3 \; R^4 & R^3 \; R^4 \\ | \; | & \diagdown \diagup \\ -CH-CH-, & -CH_2-C-CH_2-, \end{array}$$

$$\begin{array}{cc} R^3 & R^4 \\ | & | \\ -CH-CH_2-CH-, & \text{or} \; -CH_2-C-CH_2-, \\ & \quad \|\\ & \quad CH_2 \end{array}$$

when
$R^1$ and $R^2$ together represent $$\begin{array}{cc} R^3 \; R^4 & R^3 \; R^4 \\ | \; | & \diagdown \diagup \\ -CH-CH-, & -CH_2-C-CH_2-, \end{array}$$

$$\begin{array}{cc} -CH-CH_2-CH- & \text{or} \; -CH_2-C-CH_2- \\ | \qquad \qquad | & \qquad \qquad \| \\ R^3 \qquad \quad R^4 & \qquad \qquad CH_2 \end{array}$$

or
A represents $$\begin{array}{cc} R^3 \; R^4 & R^3 \; R^4 \\ | \; | & \diagdown \diagup \\ -CH-CH-, & -CH_2-C-CH_2-, \end{array}$$

$$\begin{array}{cc} R^3 & R^4 \\ | & | \\ -CH-CH_2-CH-, & -CH_2-C-CH_2- \\ & \quad \| \\ & \quad CH_2 \end{array}$$

$-CH_2-CH=CH-CH_2-$ or $-(CH_2)_4-$ when
$R^1$ and $R^2$ represent a phenyl radical which is unsubstituted or optionally substituted once or several times by chlorine, bromine, a nitro, trifluoromethyl or alkoxy group having 1 to 4 C atoms, or a carbalkoxy group having 1 to 4 C atoms, $R^3$ and $R^4$, which can be identical or different, denote hydrogen, $C_1$-$C_4$-alkyl or phenyl or together represent $-(CH_2)_m-$ with $m=2, 3, 4$ or 5, has now been found and is characterized in that dichloromethane derivatives of the formula $$(R^5O)_2CCl_2 \quad (II)$$

in which
$R^5$ represents a phenyl radical which is unsubstituted or optionally substituted once or several times by chlorine, bromine, a nitro, trifluoromethyl or alkoxy group having 1 to 4 C atoms, or a carbalkoxy group having 1 to 4 C atoms,
are reacted with aliphatic diols of the formula $$HO-A-OH \quad (III)$$

in which
A has the abovementioned meaning, in the presence of stoichiometric amounts of organic N-containing bases.

The process according to the invention is particularly suitable for the preparation of aliphatic spiroorthocarbonates. For the preparation of aliphatic spiroorthocarbonates of the formula $$\begin{array}{c}\diagup O \diagdown \diagup O \diagdown \\ B \diagdown O \diagup \diagdown O \diagup B \end{array} \quad (IV)$$

in which
B represents $$\begin{array}{cc} R^3 \; R^4 & R^3 \; R^4 \\ | \; | & \diagdown \diagup \\ -CH-CH-, & -CH_2-C-CH_2-, \end{array}$$

$$\begin{array}{cc} R^3 & R^4 \\ | & | \\ -CH-CH_2-CH- & \text{or} \; -CH_2-C-CH_2- \; \text{and} \\ & \quad \| \\ & \quad CH_2 \end{array}$$

$R^3$ and $R^4$, which can be identical or different, denote hydrogen, $C_1$-$C_4$-alkyl or phenyl or together represent $-(CH_2)_m-$, with $m=2, 3, 4$ or 5, dichloromethane derivatives of the formula $(R^5O)_2CCl_2$ (II)

in which
R⁵ represents a phenyl radical which is unsubstituted or optionally substituted once or several times by chlorine, bromine, a nitro, trifluoromethyl or alkoxy group having 1 to 4 C atoms, or a carbalkoxy group having 1 to 4 C atoms,
are reacted with aliphatic diols of the formula

HO—B—OH (V)

in which
B has the abovementioned meaning, in the presence of stoichiometric amounts of N-containing bases, which contain the nitrogen as part of an aromatic system.

In addition, the process according to the invention is suitable for the preparation of new, cyclic orthocarbonic esters of the formula

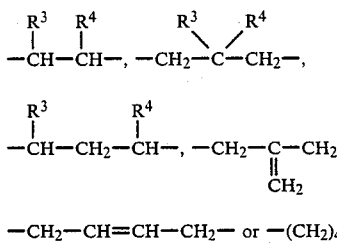

(VI)

in which
D represents

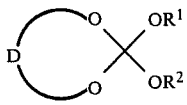

—CH₂—CH=CH—CH₂— or —(CH₂)₄—,

R¹ and R² represent a phenyl radical which is unsubstituted or is optionally substituted once or several times by chlorine, bromine, a nitro, trifluoromethyl or alkoxy group having 1 to 4 C atoms, or a carbalkoxy group having 1 to 4 C atoms,
and
R³ and R⁴, which can be identical or different, denote hydrogen, $C_1$–$C_4$-alkyl or phenyl or together represent —(CH₂)$_m$—, with m=2, 3, 4 or 5.

For the preparation of the new, cyclic orthocarbonic esters of the formula (VI), dichloromethane derivatives of the general formula $(R^5O)_2CCl_2$ (II)

in which
R⁵ represents a phenyl radical which is unsubstituted or optionally substituted once or several times by chlorine, bromine, a nitro, trifluoromethyl or alkoxy group having 1 to 4 C atoms or a carbalkoxy group having 1 to 4 C atoms,
are reacted with aliphatic diols of the formula

HO—D—OH (VII)

in which
D has the abovementioned meaning, in the presence of stoichiometric amounts of aliphatic tertiary amines.

Examples which may be mentioned of compounds of the general formula (II) are: diaryloxymethane dichlorides substituted in the aromatic rings, such as bis-(2,5-dichlorophenoxy)-methane dichloride, bis-(4-chlorophenoxy)-methane dichloride, bis-(4-nitrophenoxy)-methane dichloride, bis-(3-nitrophenoxy)-methane dichloride, bis-(3-methylphenoxy)-methane dichloride and bis-(4-methylphenoxy)-methane dichloride, and the unsubstituted parent, diphenoxymethane dichloride. Diphenoxymethane dichloride is particularly preferably used (II, R⁵=C₆H₅).

Examples of aliphatic diols of the formula (III) which can be used for the preparation of cyclic, aliphatic orthocarbonic esters of the general formula (I) and may be mentioned are: glycol, 1,2-propanediol, 2,3-butanediol, 1,3-propanediol, 2-phenyl-1,3-propanediol, 1,1-cyclohexanedimethanol, 2,2-dimethyl-1,3-propanediol, 1,3-butanediol, 2,4-pentanediol, 2-butene-1,4-diol and 1,4-butanediol; glycol, 1,2-propanediol, 1,3-propanediol, 2-methylene-1,3-propanediol, 2,2-dimethyl-1,3-propanediol, 2-butene-1,4-diol and 1,4-butanediol are particularly preferably used. The diols are used in stoichiometric amounts or in excess (about 10 to 100% excess); use in stoichiometric amounts is preferred.

In the case of the preparation of aliphatic spirocarbonates of the formula (IV), the hydrochloric acid being produced in the reaction with the dichloromethane derivative (II) is bound to N-containing bases which contain the nitrogen as part of an aromatic system. Examples which can be used for this purpose are: pyridine, which can optionally also be substituted once or several times by chlorine, bromine, a nitro, trifluoromethyl or alkoxy group having 1 to 4 carbon atoms, or a carbalkoxy group having 1 to 4 carbon atoms, quinoline, isoquinoline, quinazoline, pyrimidine and N-alkylimidazole, such as N-methylimidazole. The N-containing bases are used in stoichiometric amounts or in excess (about 10 to 100% excess), use of stoichiometric amounts preferred.

The reaction according to the invention of dichloromethane derivatives of the general formula (II) with the diols of the general formula (V) is preferably carried out in inert solvents. Examples of suitable solvents for this purpose are aromatic compounds, such as toluene and/or xylene, halogenated hydrocarbons, such as methylene chloride, ethylene chloride and/or chlorobenzene, or ethers, such as diethyl ether, tetrahydrofuran and/or anisole.

The process according to the invention for the preparation of the cyclic, aliphatic orthocarbonic esters of the formula (I) is generally carried out at temperatures of about 0° to 60° C., preferably 10° to 40° C.

The working up of the reaction mixture after the process according to the invention for the preparation of cyclic aliphatic orthocarbonic esters, in particular for the preparation of aliphatic spiroorthocarbonates of the formula (IV), can be carried out, for example, in such a manner that the resulting hydrochloride (when it is insoluble in the selected solvent) is filtered off or removed by aqueous extraction. The resulting phenol can be removed by extraction by shaking with half-concentrated or dilute aqueous alkali metal hydroxide solution or by distillation by removal of the solvent used.

The residue remaining after removal of the hydrochloride, phenol and solvent contains the desired product; the latter can be isolated either by distillation or by crystallization from a suitable inert solvent. Examples of suitable inert solvents are esters, such as ethyl acetate, or alcohols, such as methanol and/or ethanol.

In the case of the preparation of the new cyclic orthocarbonic esters of the formula (VI), the hydrochloric acid which is being produced in the reaction of diols of the formula (VII) with the dichloromethane derivative (II) is bound to a tertiary aliphatic amine. Examples which can be used for this purpose are: triethylamine, 1,4-diazabicyclo-(2,2,2)-octane, 1,5-diazabicyclo-(4,3,0)-non-5-ene, 1,5-diazabicyclo-(5,4,0)-undec-7-ene and N,N'-dimethylpiperazine; triethylamine is particularly preferred. The tertiary amines are normally used in stoichiometric amounts or in excess (about 10 to 100% excess); the use of stoichiometric amounts is preferred.

In the case of the preparation of new cyclic orthocarbonic esters of the formula (VI) with $D = -CH_2CH=CHCH_2-$ and $-(CH_2)_4-$, it is also possible to use as agents to capture hydrogen chloride the bases used for the preparation of compounds of the general formula (IV) from diols of the formula (V).

It is possible to prepare, in the sense of U.S. Pat. Nos. 4,070,347 and 4,079,038, from the new, cyclic orthocarbonic esters of the formula (VI) plastics and coatings, which are also suitable for the release of active compounds.

The examples which follow are intended to illustrate the process according to the invention.

EXAMPLES 1 TO 5

(general preparation procedure for spiroorthocarbonates of the formula (IV)

0.1 mol of dichlorodiphenoxymethane (II, $R^5 = C_6H_5$) were dissolved in 50 ml of dichloromethane and added dropwise, while stirring, to a mixture of 0.2 mol of diol of the general formula (V) and 0.2 mol of pyridine in 50 ml of dichloromethane at 20° to 25° C. (cooling with ice-water). After having been stirred at 20° C. for one hour, the organic phase was successively extracted once with 50 ml of water, once with 40 ml of half-concentrated aqueous sodium hydroxide solution and twice with 50 ml of water each time. After drying over Na$_2$SO$_4$, the solvent was removed under water pump vacuum and the residue was recrystallized from ethyl acetate.

1. Product: IV, $B = -(CH_2)_3-$, yield: 90%
2. Product: IV, $B = -CH_2-C(CH_3)_2-CH_2-$, yield: 90%
3. Product: IV,

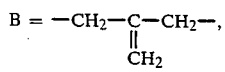

yield: 85%
4. Product: IV,

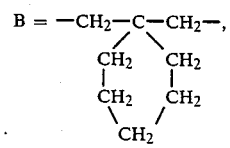

yield: 90%
5. Product: IV, $B = -CH_2-CH_2-$, yield: 75%

The physical data of the products from examples 1 to 5 agree with the data given in the literature.

EXAMPLES 6 TO 9

0.12 mol of diol of the general formula (VII) and 0.1 mol of triethylamine were initially introduced into 50 ml of dichloromethane, and a solution of 0.1 mol of dichlorodiphenoxymethane (II, $R^5 = C_6H_5$) in 50 ml of dichloromethane was added dropwise, with stirring, at 18° to 20° C. After-reaction at room temperature for 2 hours.

The solution was extracted twice with 50 ml of water each time, and the organic phase was dried over Na$_2$SO$_4$. The residue remaining after removal of the solvent under water pump vacuum was recrystallized from ethyl acetate or methanol.

6. Product: VI, $D = -(CH_2)_3-$, $R^1, R^2 = C_6H_5$; melting point 96°-97° C., yield: 95%
7. Product: VI, $D = -CH_2-C(CH_3)_2-CH_2-$, $R^1, R^2 = C_6H_5$; melting point 99°-100° C., yield: 95%
8. Pyridine was used instead of triethylamine as the base. Product: VI, $D = -CH_2-CH=CH-CH_2-$, $R^1, R^2 = C_6H_5$; melting point 71°-72° C., yield: 95%.
9. Pyridine was used instead of triethylamine as the base. Product: VI, $D = -(CH_2)_4-$, $R^1, R^2 = C_6H_5$; melting point 82°-84° C., yield: 95%.

What is claimed is:
1. A process for the preparation of an aliphatic spiroothocarbonate of the formula

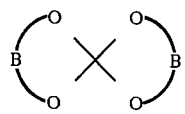

in which
B represents

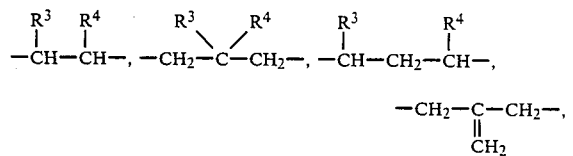

$-CH_2-CH_2-$ or $-CH_2-CH_2-CH_2-$
and
R$^3$ and R$^4$, which can be identical or different, denote hydrogen, C$_1$-C$_4$-alkyl or phenyl or together represent $-(CH_2)_m-$, with the proviso that R$^3$ and R$^4$ cannot simultaneously denote hydrogen, with m=2, 3, 4 or 5, wherein a dichloromethane derivative of the formula $(R^5O)_2CCl_2$
in which
R$^5$ represents a phenyl radical which is unsubstituted or optionally substituted once or several times by chlorine, bromine, a nitro, trifluoromethyl or alkoxy group having 1 to 4 C atoms, or a carbalkoxy group having 1 to 4 C atoms, is reacted with an aliphatic diol of the formula HO—B—OH
in which
B has the abovementioned meaning, in the presence of a stoichiometric amount of a N-containing base, which contains the nitrogen as part of an aromatic system said base being pyridine, which can optionally also be substituted once or several times by chlorine, bromine, a nitro, trifluoromethyl or alkoxy group having 1 to 4 carbon atoms, or a carbalkoxy group having 1 to 4 carbon atoms, quinoline, isoquinoline, quinazoline, pyrimidine and N-alkylimidazole.

* * * * *